United States Patent [19]

van Andel

[11] Plant 5,208

[45] Mar. 20, 1984

[54] ALSTROEMERIA CULTIVAR NAMED STALLUC

[75] Inventor: Jacob van Andel, Aalsmeer, Netherlands

[73] Assignee: M. C. B. V. Handelskweke M. C. van Staaveren, Aalsmeer, Netherlands

[21] Appl. No.: 416,842

[22] Filed: Sep. 13, 1982

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Chas. W. Rummler

[57] ABSTRACT

A new alstroemeria cultivar characterized by its bright purple flower, the inner petals of which have a light yellow base over which short brown pencil stripe spots appear in longitudinal rows extending substantially to the tip of the petals, by its substantially continuous year-around profuse production of medium sized blooms, and by its vigorous upright growth habit with numerous blossoms in compound umbel arrangement at the top of a strong upright stem of about 1.50 m. in length.

1 Drawing Figure

BACKGROUND OF THE INVENTION

This new alstroemeria cultivar originated as a seedling produced by my crossing of selected plants from breeding stock maintained in greenhouse at Aalsmeer, Holland with the object of producing a plant which would flower all year around with blossoms having a more bluish coloration than heretofore obtained. This particular plant was selected for propagation and test because of its bluish-purple coloration and its apparently vigorous growth habit and profuse production of flowers. Propagation of this plant is done by dividing root stocks and propagation through several successive generations at Aalsmeer has demonstrated that the novel characteristics of this cultivar hold true from generation to generation and appear to be firmly fixed.

DESCRIPTION OF THE DRAWING

This new variety of alstroemeria plant is illustrated by the accompanying photographic drawing which in full color shows the nature of the inflorescense both in flower form and arrangement, the color rendition being as nearly true as it is reasonably possible to obtain by conventional professional photographic procedures.

DESCRIPTION OF THE NEW PLANT

The following is a detailed description of my new alstroemeria plant with color designations according to the R.H.S. Colour Chart of The Royal Horticultural Society of London, England, the photograph having been made in greenhouse during the spring blooming season at Aalsmeer, Holland.

THE PLANT

Origin: Seedling.

Parentage:

*Seed parent.*—No. 2159-3 (Unpatented).

*Pollen parent.*—No. 6D1 (Unpatented).

The parents of this seedling are included in a collection maintained for breeding purposes, each plant being appropriately identified by numbers recorded in the permanent records of B. V. Handelskwekerij, M. C. van Staaveren at Aalsmeer, Holland.

Classification:

*Botanic.*—Alstroemeria.

*Commercial.*—Alstroemeria Cultivar.

Form: A tall, slender flowering stalk with flower bearing branches in compound umbel arrangement at its top.

Height: About 150 cm.

Growth: Vigorous, upright and strong.

Root stock: Tuberous. The tubers bear many buds during the year from which the flower stalks grow in various stages of development during the course of the year.

Branching: Each flower stalk branches at the top into a compound umbel having about 7 flower bearing stems.

Foliage:

*Quantity.*—Medium with 20 to 30 leaves per stem. Size of leaf varies depending on season.

Leaf shape: Elliptic.

Texture: Leathery.

Color:

*Upper side.*—Dark Green.

*Under side.*—Medium Green.

Rizomes: Size varying with the season.

*Color.*—White.

THE BUD

Form: Pear-shaped.

Size: Medium.

*Diameter.*—About 1.5 cm. and length about 4 to 4.5 cm.

Rate of opening: Normal. There is no calyx and the 6 petals are perianth.

Peduncle:

*Length.*—About 2.5 to 3 cm.

*Character.*—The peduncle is erect and rigid and makes an angle of about 30 degrees with the stem.

THE FLOWER

Blooming habit: Continuous, blooming profusely from season to season throughout the year.

Flower size: Medium.

*Diameter.*—About 5.5 cm.

*Depth.*—About 5 cm.

Borne: Singly on a relatively short peduncle.

Shape: Cup-shaped when bloom first opens becoming generally funnel-like as bloom matures.

Petalage:

*Number of petals.*—6.

*Arrangement.*—Two concentric circles each of 3 petals.

*Form.*—Broad ovate.

Texture: Soft.

Appearance: Shiny.

Color:

*Outer petals.*—80B; Reverse Side — 80C.

*Inside petals.*—Body 80B; Reverse Side 80D.

Flower stem:

*Length.*—About 150 cm.

[Character.—Straight and strong.

*Color.*—Medium Green.

Persistence: The flowers hang on and dry.

Fragrance: None.

Lasting quality:

*On plant.*—15 to 20 days.

*As a cut flower.*—10 to 15 days.

REPRODUCTIVE ORGANS

Stamens:

*Number.*—Six — arrangement — a stamen opposite each petal.

*Anthers.*—Approximately 1 cm. long. Color: Gray/Green.

*Filaments.*—Length — approximately 4 cm. Color: Purple.

*Pollen.*—Blue.

Pistils:

*Number.*—1.

*Style.*—Length — 7 mm.

*Color.*—Purple.

*Stigmas.*—Color — purple.

FRUIT

Shape: Capsular.

Fertile: The fruit is fertile.

Color at maturity: Light Brown.

This new alstroemeria cultivar is particularly distinguished by the bluish-purple coloration of its blossoms, the straight, sturdy and upright flowering stem, and the relatively short, sturdy peduncle for each of the flowers.

I claim:

1. A new and distinct alstroemeria cultivar substantially as herein shown and described, characterized by the distinctive bluish-purple coloring of the flowers, and by the light yellow coloring toward the base of each of the inside petals and the bright longitudinally extending pencil stripes on the base of each inside petal to near the tip end thereof.

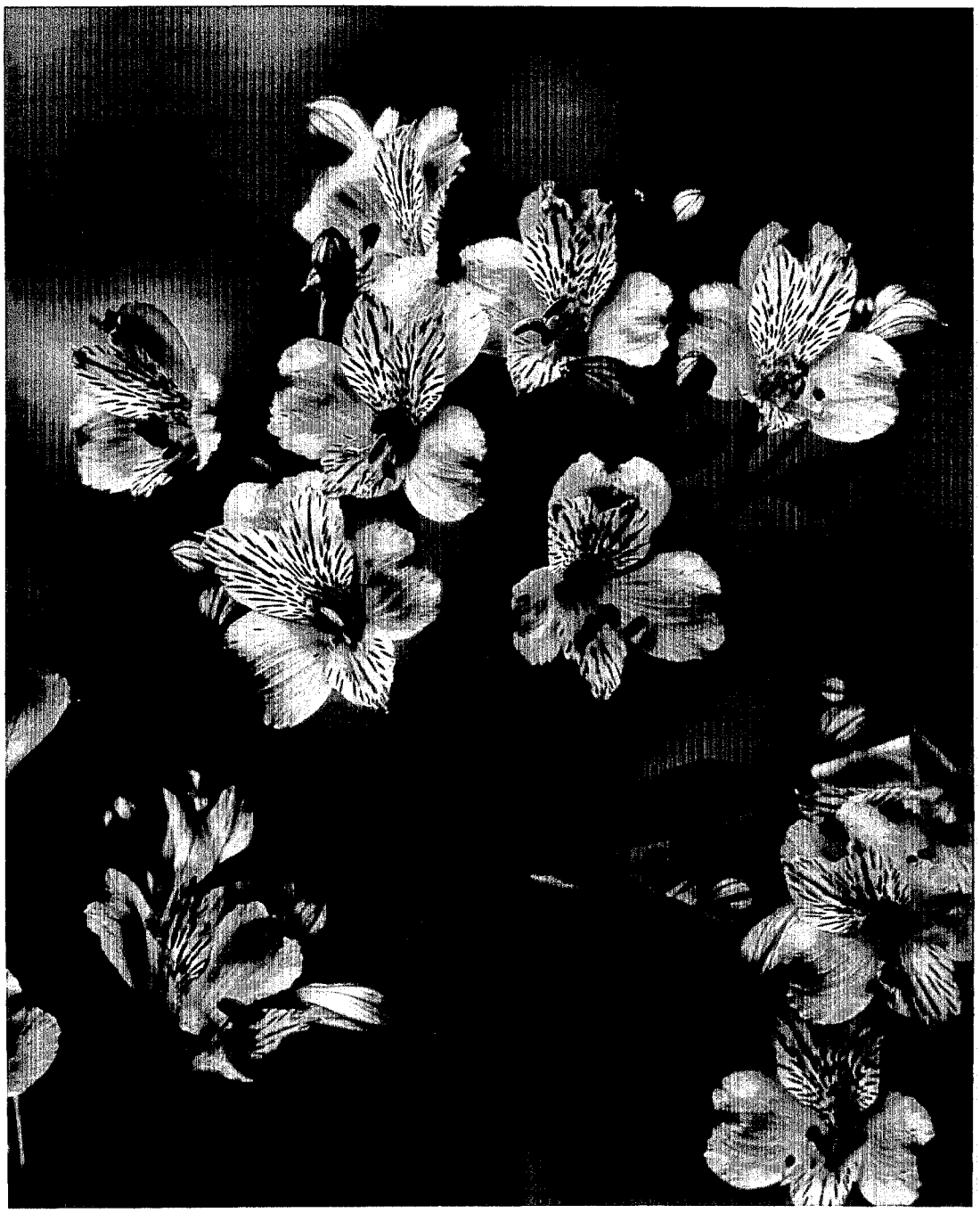

* * * * *